United States Patent [19]

Krüger et al.

[11] Patent Number: 4,470,934
[45] Date of Patent: Sep. 11, 1984

[54] PREPARATION OF CYANOALKYLPHOSPHORIC ACID ESTER CHLORIDES

[75] Inventors: Bernd-Wieland Krüger; Hans-Joachem Riebel, both of Wuppertal; Ingeborg Hammann, Cologne; Berhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 475,274

[22] Filed: Mar. 14, 1983

Related U.S. Application Data

[62] Division of Ser. No. 344,263, Jan. 28, 1982.

[30] Foreign Application Priority Data

Feb. 21, 1981 [DE] Fed. Rep. of Germany ....... 3106497

[51] Int. Cl.³ .......................... C07F 9/146; C07F 9/20
[52] U.S. Cl. ................................... 260/968; 260/940; 549/6; 549/218; 549/220
[58] Field of Search ...................... 260/972, 961, 940; 549/6, 218, 220

[56] References Cited

FOREIGN PATENT DOCUMENTS 72482 2/1983 European Pat. Off. .
3106497 9/1982 Fed. Rep. of Germany .

OTHER PUBLICATIONS

Shishkin et al, "Chem. Abst.", vol. 89, (1978) 24457t.
Kabachnik et al, "Chem. Abst.", vol. 48, (1951) 6569i.

*Primary Examiner*—Anton H. Sutto
*Attorney, Agent, or Firm*—Sprung Horn Kramer & Woods

[57] ABSTRACT

New cyanoalkylphosphoric acid ester chlorides of the general formula

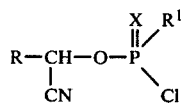

in which
R represents a hydrogen atom, an optionally substituted radical selected from alkyl, alkenyl, alkinyl, cycloalkyl, cycloalkenyl, aralkyl, aralkenyl and aryl, or an optionally substituted heterocyclic radical,
$R^1$ represents an optionally substituted radical selected from alkyl, alkenyl, alkinyl, aryl, aralkyl, alkoxy, aryloxy, aralkoxy, alkylthio, alkenylthio, alkinylthio, arylthio, aralkylthio, alkylamino (monoalkylamino or dialkylamino), arylamino or aralkylamino
and X represents oxygen or sulphur
are obtained by the reaction of a phosphoric acid dichloride of the general formula

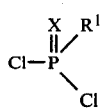 (II)

with an aldehyde of the general formula

R—CHO      (III)

in the presence of an approximately equimolar quantity of a water-soluble cyanide. The compounds of the formula (I) can be used as intermediate products for the preparation of insecticides.

15 Claims, No Drawings

PREPARATION OF CYANOALKYLPHOSPHORIC ACID ESTER CHLORIDES

This is a division of application Ser. No. 344,263, filed Jan. 28, 1982.

The invention relates to certain new cyanoalkylphosphoric acid ester chlorides, to an unobvious process for their production, and to their use as intermediate products for the preparation of pesticidal phosphoric acid derivatives.

It is already known that certain pesticidal cyanohydrin phosphates are obtained if appropriate phosphoric acid ester chlorides are reacted with cyanohydrins (α-hydroxycarboxylic acid nitriles) (see German Published Specifications Nos. 1,047,776 and 1,224,307). However, this method of preparation is only of limited use for this purpose, owing to the lack of suitable starting compounds or because of unsatisfactory possible methods of preparation. There is, therefore, a demand for new intermediate products for cyanohydrin phosphates.

According to the present invention we provide, as new compounds, cyanoalkylphosphoric acid ester chlorides of the general formula

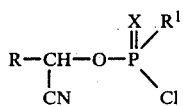

(I)

in which
R represents a hydrogen atom, an optionally substituted radical selected from alkyl, alkenyl, alkinyl, cycloalkyl, cycloalkenyl, aralkyl, aralkenyl and aryl, or an optionally substituted heterocyclic radical,
$R^1$ represents an optionally substituted radical selected from alkyl, alkenyl, alkinyl, aryl, aralkyl, alkoxy, aryloxy, aralkoxy, alkylthio, alkenylthio, alkinylthio, arylthio, aralkylthio, alkylamino (monoalkylamino or dialkylamino), arylamino or aralkylamino, and
X represents an oxygen or sulphur atom.

According to the present invention we further provide a process for the production of a compound of the present invention, characterized in that a phorphoric acid dichloride of the general formula

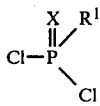

(II)

in which $R^1$ and X have the meanings given above, is reacted with an aldehyde of the general formula

 R—CHO     (III)

in which R has the meaning given above, in the presence of an approximately equimolar quantity of water-soluble cyanide, in the presence of water and organic solvents which are virtually immiscible with water and, if appropriate, in the presence of a catalyst, at a temperature between 0° and 80° C.

It is surprising that the new cyanoalkylphosphoric acid ester chlorides are obtained in good yields and in high purity by the process according to the invention, since it was to be expected that the products of the formula (I) would react further, with substitution of the chlorine atom.

Optionally substituted alkyl of R and $R^1$ are straight-chain or branched alkyl having preferably 1 to 20, more preferably 1 to 10, particularly 1 to 5, carbon atoms. Optionally substituted methyl, ethyl, n-propyl, iso-propyl, n-butyl, isobutyl and tertiary-butyl may be mentioned as examples.

Optionally substituted alkenyl of R and $R^1$ or alkenylthio $R^1$ are straight-chain or branched radicals having preferably 2 to 5, particularly 2 to 4, carbon atoms. Optionally substituted ethenyl, prop-1-enyl, prop-2-enyl and but-3-enyl and the respective thio-radicals may be mentioned as examples.

Optionally substituted alkinyl of R and $R^1$ or alkinylthio $R^1$ are straight-chain or branched radicals having preferably 2 to 5, particularly 2 to 4, carbon atoms. Optionally substituted ethinyl, prop-1-inyl, prop-2-inyl and but-3-inyl and the respective thio-radicals may be mentioned as examples.

Optionally substituted cycloalkyl of R is monocyclic, bicyclic and tricyclic cycloalkyl having preferably 3 to 8, particularly 3, 5 or 6, carbon atoms. Optionally substituted cyclopropyl, cyclobutyl, cyclopentyl, cyclohexyl, cycloheptyl, bicyclo[2,2,1]heptyl, bicyclo[2,2,2] octyl and adamantyl may be mentioned as examples.

Optionally substituted cycloalkenyl of R is preferably monocyclic cycloalkenyl having 5 or 6 carbon atoms and 1 or 2 double bonds.

Optionally substituted alkoxy of $R^1$ is straight-chain or branched alkoxy having preferably 1 to 6, particularly 1 to 4, carbon atoms. Optionally substituted methoxy, ethoxy, n-propoxy, isopropoxy, n-butoxy, isobutoxy and tertiary-butoxy may be mentioned as examples.

Optionally substituted alkylthio of $R^1$ is straight-chain or branched alkylthio having preferably 1 to 6, particularly 1 to 4, carbon atoms. Optionally substituted methylthio, ethylthio, n-propylthio, isopropylthio, n-butylthio, isobutylthio and tertiary-butylthio may be mentioned as examples.

Optionally substituted aryl of R and $R^1$ are aryl having preferably 6 to 10 carbon atoms in the aryl part. Optionally substituted phenyl or naphthyl, particularly phenyl, may be mentioned as examples.

Optionally substituted aralkyl of R and $R^1$ are aralkyl which is optionally substituted in the aryl part and/or alkyl part and which has preferably 6 or 10, particularly 6, carbon atoms in the aryl part and preferably 1 to 4, particularly 1 or 2, carbon atoms in the alkyl part, it being possible for the alkyl part to be straight-chain or branched. Optionally substituted benzyl and phenylethyl may be mentioned as examples.

Optionally substituted aralkenyl of R, corresponds in its aryl part to the aralkyl radical R. It contains, in the alkenyl part, preferably 2 to 6, particularly 2 or 3, carbon atoms and 1 or 2, preferably 1, double bond.

Optionally substituted aryloxy, arylthio and arylamino of $R^1$ preferably contain 6 or 10 carbon atoms in the aryl part, phenyloxy, naphthyloxy, phenylthio, naphthylthio, phenylamino and naphthylamino, preferably phenyloxy, phenylthio and phenylamino, being mentioned.

Optionally substituted aralkoxy, aralkylthio and aralkylamino of $R^1$ preferably contain 5 or 10 carbon atoms in the aryl part, phenyl being mentioned as particularly preferred. The alkyl part is branched or straight-chain and contains preferably 1 to 4, particularly 1 or 2, carbon atoms. The benzyl radical is particularly preferred as the aralkyl part.

In the optionally substituted alkylamino of $R^1$, the amino group contains 1 or 2 alkyl groups, each of which can be straight-chain or branched and preferably contains 1 to 5, particularly 1 to 3, carbon atoms, methyl, ethyl, n-propyl and isopropyl being mentioned. Monomethylamino and dimethylamino may be quoted as examples.

Optionally substituted heterocyclic radicals of R are generally heteroparaffinic, heteroaromatic and heteroolefinic 5-membered to 7-membered, preferably 5-membered or 6-membered, rings having preferably 1 to 3, particularly 1 or 2, identical or different heteroatoms. Heteroatoms are oxygen, sulphur, or nitrogen. Optionally substituted pyrrolidinyl, piperidinyl, furyl, thiophenyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,3,4-oxadiazolyl, 1,2,4-oxadiazolyl, 1,2,5-oxadiazolyl, azepinyl, pyrrolyl, pyridyl, piperazinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,3,6-oxazinyl, 1,2,6-oxazinyl, oxepinyl, thiepinyl and 1,2,4-diazepinyl may be mentioned as examples.

The substituted radicals mentioned in the definition of R and $R^1$ can carry one or several, preferably 1 to 3, particularly 1 or 2, identical or different substitutents. The following may be quoted as examples of substituents: alkyl having preferably 1 to 4, particularly 1 or 2, carbon atoms, such as methyl, ethyl, n-propyl, isopropyl, n-butyl, isobutyl and tertiary-butyl; alkoxy having preferably 1 to 4, particularly 1 or 2, carbon atoms, such as methoxy, ethoxy, n-propyloxy, isopropyloxy, n-butyloxy, isobutyloxy and tertiary-butyloxy; alkylthio having preferably 1 to 4, particularly 1 or 2, carbon atoms, such as methylthio, ethylthio, n-propylthio, isopropylthio, n-butylthio, isobutylthio and tertiary-butylthio; alkylamino having 1 or 2 alkyl groups each of which contains preferably 1 to 4, particularly 1 or 2, carbon atoms, such as monomethylamino, dimethylamino, monoethylamino and diethylamino; halogenoalkyl, halogenalkylthio and halogenoalkoxy having preferably 1 to 4, particularly 1 or 2, carbon atoms and preferably 1 to 5, particularly 1 to 3, halogen atoms, the halogen atoms being identical or different and preferably being fluorine, chlorine or bromine, particularly fluorine, such as trifluoromethyl, trifluoromethoxy and trifluoromethylthio; halogen, preferably fluorine, chlorine, bromine and iodine, particularly chlorine and bromine; nitro; and alkoxycarbonyl having preferably 2 to 4, particularly 2 or 3, carbon atoms, such as methoxycarbonyl, ethoxycarbonyl and phenoxybenzyloxycarbonyl. In the case of radicals containing aryl parts, the aryl parts, for example the phenyl rings, can be substituted by alkylenedioxy groups which preferably contain 1 to 3, particularly 1 or 2, carbon atoms and can be substituted by 1 to 4 identical or different halogen atoms (fluorine, chlorine, bromine or iodine).

Halogen denotes (where not otherwise described) fluorine, chlorine, bromine or iodine, preferably fluorine, chlorine or bromine.

Compounds of the formula (I), in which
R represents a hydrogen atom, an alkyl radical which is optionally substituted by halogen, $C_1$ to $C_4$ alkoxy, $C_1$ to $C_4$ alkylthio or $C_1$ to $C_4$ alkylamino and which has 1 to 20 carbon atoms, an optionally halogen-substituted $C_2$ to $C_5$ alkenyl or $C_2$ to $C_5$ alkinyl radical, a $C_3$ to $C_8$ cycloalkyl radical which is optionally substituted by $C_1$ to $C_4$ alkyl, $C_1$ to $C_4$ alkoxycarbonyl, phenoxybenzyloxycarbonyl and/or halogen, a phenyl-$C_1$ to $C_4$ alkyl radical which is optionally substituted by halogen, optionally halogen substituted $C_1$ to $C_4$ alkyl or optionally halogen substituted $C_1$ to $C_4$ alkoxy, a phenyl radical which is optionally substituted by halogen, nitro, $C_1$ to $C_4$ alkyl, optionally halogen-substituted $C_1$ to $C_4$ alkoxy, optionally halogen-substituted $C_1$ to $C_4$ alkylthio or trifluoromethyl and/or by optionally halogen-substituted $C_1$ or $C_2$ alkylenedioxy, or represents a furyl, thienyl or pyridyl radical,
$R^1$ represents an optionally halogen-substituted radical selected from $C_1$ to $C_5$ alkyl, $C_2$ to $C_5$ alkenyl, $C_2$ to $C_5$ alkinyl, phenyl, benzyl, $C_1$ to $C_5$ alkoxy, phenoxy, benzyloxy, $C_1$ to $C_5$ alkylthio, $C_2$ to $C_5$ alkenylthio, $C_2$ to $C_5$ alkinylthio, phenylthio, benzylthio, $C_1$ to $C_5$ alkylamino (monoalkylamino or dialkylamino), phenylamino or benzylamino, and
X represents oxygen or sulphur,
are preferred compounds of the present invention and preferred products of the process according to the invention.

Particularly preferred compounds of the present invention are those in which
R represents a hydrogen atom, an alkyl radical which is optionally substituted by fluorine, chlorine, methoxy, methylthio or dimethylamino and which has 1 to 10 carbon atoms, a $C_2$ to $C_5$ alkenyl radical; a $C_3$ to $C_6$ cycloalkyl radical which is optionally substituted by chlorine and/or methyl; a phenyl-$C_1$ or $C_2$ alkyl radical which is optionally substituted by chlorine or trifluoromethoxy, a phenyl radical which is optionally substituted by fluorine, chlorine, nitro, methyl, methoxy, trifluoromethoxy, trifluoromethyl and/or methylenedioxy, or a thienyl or pyridyl radical,
$R^1$ represents an optionally fluorine-substituted or optionally chlorine-substituted radical selected from $C_1$ to $C_5$ alkyl, phenyl, $C_1$ to $C_5$ alkoxy, phenoxy, benzyloxy, $C_1$ to $C_5$ alkoxy, phenoxy, benzyloxy, $C_1$ to $C_5$ alkylthio, phenylthio, benzylthio and $C_1$ to $C_5$ alkylamino (monoalkylamino or dialkylamino), and
X represents oxygen or sulphur.

Halogen denotes fluorine, chlorine, bromine or iodine, preferably fluorine, chlorine or bromine.

If, for example, methanethiophosphonic acid dichloride, acetaldehyde and sodium cyanide are used as starting materials in the process according to the invention, the reaction of these compounds can be described by the following equation:

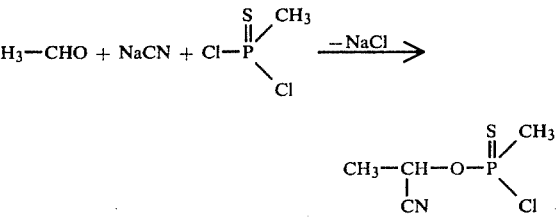

Preferred phosphoric acid dichlorides of formula (II) to be used as starting materials in the process according to the invention are those in which X and $R^1$ represent those radicals which are given above in the definition of the preferred and particularly preferred compounds of formula (I).

The following may be mentioned as examples of the compounds of the formula (II):

methanephosphonic acid dichloride, ethanephosphonic acid dichloride, propanephosphonic acid dichloride, butanephosphonic acid dichloride and benzenephosphonic acid dichloride, as well as the corresponding thiono analogues; methylphosphoric acid ester dichloride, ethylphosphoric acid ester dichloride, n-propylphosphoric acid ester dichloride, isopropylphosphoric acid ester dichloride, n-butylphosphoric acid ester dichloride, isobutylphosphoric acid ester dichloride, sec-butylphosphoric acid ester dichloride, phenylphosphoric acid ester dichloride and benzylphosphoric acid ester dichloride, as well as the corresponding thiono analogues; and methylthiolphosphoric acid ester dichloride, ethylthiolphosphoric acid ester dichloride, n-propylthiolphosphoric acid ester dichloride, isopropylthiolphosphoric acid ester dichloride, n-butylthiolphosphoric acid ester dichloride, isobutylthiolphosphoric acid ester dichloride, sec-butylthiolphosphoric acid ester dichloride, phenylthiolphosphoric acid ester dichloride and benzylthiolphosphoric acid ester dichloride, as well as the corresponding thiono analogues.

The compounds of the formula (II) are known and/or can be prepared in a customary manner, according to processes which are in themselves known (see Methoden der organischen Chemie [Methods of organic chemistry] (Houben-Weyl-Müeller), 4th edition, volume 12/1 (1963), pages 387–406 and pages 552–557; volume 12/2 (1964), pages 212–225, 590–594 and 682–683; Thieme-Verlag-Stuttgart).

Preferred aldehydes of formula (III) which are also to be used as starting materials are those in which R represents those radicals which are given above in the definition of preferred or particularly preferred compounds of formula (I).

The following may be mentioned as examples of the compounds of the formula (III):

formaldehyde, acetaldehyde, propionaldehyde, butyraldehyde, iso-butyraldehyde, valeraldehyde, iso-valeraldehyde, sec-valeraldehyde, caproic aldehyde, iso-caproic aldehyde, sec-caproic aldehyde, pivalic aldehyde, acrolein, crotonaldehyde, methoxyacetaldehyde, methylthioacetaldehyde, cyclohexanecarbaldehyde, benzaldehyde, 4-chloro-benzaldehyde, 4-methylbenzaldehyde, 3,4-methylenedioxybenzaldehyde, 4,5-methylenedioxy-2-nitro-benzaldehyde, phenylacetaldehyde, α-phenylpropionaldehyde, thiophene-2-carbaldehyde, thiophene-3-carbaldehyde, pyridine-2-carbaldehyde and pyridine-3-carbaldehyde.

The starting compounds of the formula (III) are known.

Water-soluble cyanides which can be used in the process according to the invention are, for example, alkali metal cyanides (such as sodium cyanide and potassium cyanide); sodium cyanide is preferably used.

Straight-chain or branched alkanes or cycloalkanes having 5 to 10 carbon atoms (such as n-petane, n-hexane, n-heptane, n-octane, n-nonane, n-decane, 2-methylpentane, 3-methylpentane, 2-methylhexane, 2,2,4-trimethylpentane, cyclohexane and methylhexane) and also methylbenzenes (such as toluene or xylenes), as well as mixtures of these hydrocarbons, are preferably employed as the water-immiscible solvent in the process according to the invention.

Compounds which are customarily employed for the phase transfer of reactants in reactions in two-phase systems comprising water and water-immiscible organic solvents are preferably used as the catalysts in the process according to the invention. Tetraalkylammonium salts and trialkyl-aralkyl-ammonium salts having preferably 1 to 10, particularly 1 to 8, carbons per alkyl group, preferably phenyl as the aryl constituent of the aralkyl group and preferably 1 to 4, particularly 1 or 2, carbon atoms in the alkyl part of the aralkyl groups are especially preferred compounds of this type. The halides, such as chlorides, bromides, and iodides, preferably the chlorides and bromides, are particularly suitable in this context. Tetrabutylammonium bromide, benzyl-triethylammonium chloride and methyltrioctylammonium chloride may be mentioned as examples.

The reaction temperature is maintained at a temperature between 0° and 80° C., preferably between 0° and 30° C., in the process according to the invention. The process is preferably carried out under normal pressure.

In general, between 0.6 and 1.1 mol, preferably 0.75 to 1 mol, of aldehyde of the formula (III), between 1 and 1.5 mols, preferably 1.1 to 1.3 mols, of cyanide and, if appropriate, between 0.001 and 0.05 mol, preferably 0.01 to 0.03 mol, of the catalyst are employed per mol of phosphoric acid dichloride of the formula (II).

In a preferred embodiment of the process according to the invention, the starting compounds of the formulae (II) and (III) and the catalyst are dissolved in the water-immiscible solvent, and an aqueous solution of the cyanide is slowly added to this solution, the reaction temperature being brought to about 0° to 10° C., if necessary at first by external cooling. The complete reaction mixture is then stirred for several hours at room temperature.

The mixture is worked up by diluting, if necessary, with further water-immiscible solvent, separating off the organic phase, washing it with water, drying it and filtering it. The filtrate is freed from solvent by distillation under reduced pressure, the crude product being obtained as an oily residue.

The cyanoalkylphosphoric acid ester chlorides to be prepared by the process according to the invention can be used as intermediate products for the preparation of pesticidal phosphoric acid derivatives of the general formula

in which

X, R and $R^1$ have the meaning given above, and $R^2$ represents an optionally substituted radical selected from alkoxy, alkylthio and alkylamino preferably having 1 to 5 carbon atoms, aryloxy, arylthio and arylamino preferably having phenyl as the aryl part, and aralkoxy, aralkylthio and aralkylamino preferably having phenyl as the aryl part and preferably having 1 to 5, particularly 1 or 2, carbon atoms in the alkyl part.

The cyanoalkyl-phosphoric acid derivatives of the formula (IV) are obtained from the corresponding compound of the formula (I) by reaction with a nucleophile of the general formula $$MR^2 \quad (V)$$

in which $R^2$ has the meaning given above and

M represents hydrogen, sodium, potassium or ammonium, if appropriate in the presence of an acid-binding agent (such as triethylamine or potassium carbonate) and, if appropriate, in the presence of a diluent (such as toluene or acetonitrile) at a temperature between 10° and 100° C.

The mixture is worked up by diluting it, if necessary, with a virtually water-immiscible organic solvent (such as toluene or methylene chloride), washing it with water, drying it and filtering it. After the solvent has been distilled off under reduced pressure, the residue essentially contains the products of the formula (IV).

The compounds of the formula (IV) can be used in the form of generally customary formulations, for example emulsions, solutions, powders, granules and the like, as insecticides and acaricides. In general, these formulations contain between 0.1 and 95 per cent by weight of active compound and customary extenders and formulation auxiliaries, such as organic solvents (for example xylene and methyl ethyl ketone), ground natural minerals (such as kaolins), and surface-active compounds (such as alkylaryl polyglycol ethers). The active compound concentrations of the finished use forms are, in general, between 0.001 and 1% by weight. With the aid of the compounds of the formula (IV), insects and acaridae can be combated in the fields of plant protection, storage of products and animal husbandry.

The Examples which follow illustrate the preparation of the novel compounds of present invention.

PREPARATIVE EXAMPLES

Example 1

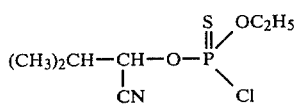

233 g (1.3 mols) of O-ethyl thiophosphoric acid ester dichloride, 72 g (1.0 mol) of isobutyraldehyde and 6 g of tetrabutylammonium bromide were initially introduced into 1 liter of hexane, and a solution of 56 g (1.1 mols) of sodium cyanide in 100 ml of water was added dropwise to the mixture at an internal temperature between 0° and 5° C., while stirring vigorously. After the addition had ended, the temperature was slowly increased to 20° C. and the mixture was stirred for a further 12 hours. The aqueous phase was then separated off, and the organic phase was washed with 100 ml of water and was dried with sodium sulphate. After the solvent had been stripped off in the vacuum from a water jet and the excess starting material had been distilled off, 173 g (72% of theory) of O-ethyl O-(1-cyano-2-methyl-propyl) thiophosphoric acid diester chloride were obtained as an oleaginous residue of refractive index $n_D^{20}$; 1.4806.

The compounds of formula (I), which are listed in the table below, could be prepared analogously:

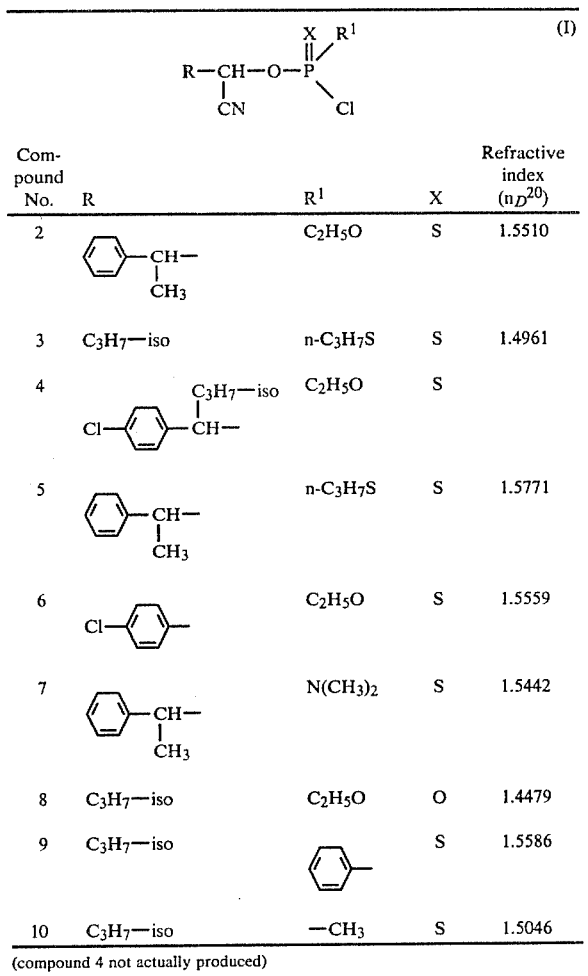

Example 2

Preparation of compounds of the formula

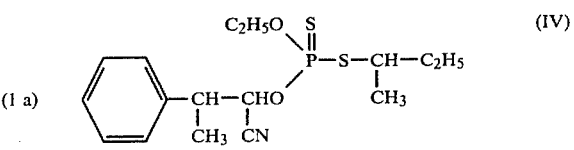

12.3 g (0.11 mol) of sodium sec-butyl-mercaptide were initially introduced into 100 ml of acetonitrile, and 30.3 g (0.1 mol) of O-ethyl O-(1-cyano-2-phenyl-propyl) thiophosphoric acid chloride, dissolved in 40 ml of acetonitrile, were slowly added dropwise at an internal temperature of 0° to 20° C. The mixture was stirred for 12 hours at 60° C. and was concentrated in the vacuum from a water jet, and the residue was taken up in methylene chloride. The organic phase was then washed twice with 50 ml of dilute sodium hydroxide solution and twice with 50 ml of water, and was then dried with sodium sulphate. After the solvent had been stripped off, 22.3 g (62% of theory) of O-ethyl O-(1-cyano-2-phenyl-propyl) S-sec-butyl dithiosphosphate were obtained as an oleaginous residue with a refractive index $n_D^{20}$:1.5600.

The compounds of the formula:

$$\underset{n\text{-}H_7C_3S}{\overset{H_3C}{\diagdown}}\overset{S}{\underset{\parallel}{P}}-O-\underset{CN}{\overset{|}{CH}}-C_3H_7-iso \qquad (2\,a)$$

and $$\underset{n\text{-}H_7C_3S}{\overset{H_5C_2O}{\diagdown}}\overset{S}{\underset{\parallel}{P}}-O-CH_2-CN \qquad (3\,a)$$

were obtained analogously.

Other compounds of formula (IV) could also be obtained in an analogous manner.

The insecticidal activity of compounds of formula (IV) is illustrated by the following example:

Example 3

Insecticidal activity of the compounds of the formula (IV)

Laphygma test
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all the caterpillars had been killed; 0% meant that none of the caterpillars had been killed.

In this test, the compounds 1a, 2a and 3a showed a destruction of 100% after 3 days, at an active compound concentration of 0.1%.

It will be understood that the specification and examples are illustrative but not limitative of the present invention and that other embodiments within the spirit and scope of the invention will suggest themselves to those skilled in the art.

We claim:

1. A process for the production of a compound of the formula $$R-\underset{CN}{\overset{|}{CH}}-O-\overset{X}{\underset{\diagdown}{P}}\overset{R^1}{\diagup}_{Cl}$$

in which
R represents a hydrogen atom, an optionally substituted radical selected from alkyl, alkenyl, alkinyl, cycloalkyl, cycloalkenyl, aralkyl, aralkenyl and aryl, or an optionally substituted heterocyclic radical,
$R^1$ represents an optionally substituted radical selected from alkyl, alkenyl, alkinyl, aryl, aralkyl, alkoxy, aryloxy, aralkoxy, alkylthio, alkenylthio, alkinylthio, arylthio, aralkylthio, alkylamino (monoalkylamino or dialkylamino), arylamino and aralkylamino, and
X represents oxygen or sulphur,
comprising reacting a phosphoric acid dichloride of the formula $$Cl-\overset{X}{\underset{\diagdown}{P}}\overset{R^1}{\diagup}_{Cl}$$

with an aldehyde of the formula

R—CHO at a temperature between about 0° and 80° C. and in the presence of an approximately equimolar quantity of a water-soluble cyanide, water and an organic solvent which is virtually immiscible with water.

2. A process according to claim 1, in which the reaction is effected in the presence of a catalyst.

3. A process according to claim 2, in which the catalyst is a tetraalkyl-aralkyl-ammonium salt or trialkyl-aralkyl-ammonium salt.

4. A process according to claim 3, in which the catalyst is tetrabutylammonium bromide.

5. A process according to claim 1, in which the reaction is carried out at a temperature between about 0° and 30° C.

6. A process according to claim 1, in which the water-soluble cyanide is sodium cyanide.

7. A process according to claim 1, in which the solvent is at least one of a straight-chain or branched alkane or cycloalkane having 5 to 10 carbon atoms or a methylbenzene.

8. A process according to claim 7, wherein the water-soluble cyanide is sodium cyanide and the reaction is carried out at a temperature between about 0° and 30° C. in the presence of tetrabutylammonium bromide as catalyst.

9. A process according to claim 9, in which
R represents a hydrogen atom, an alkyl radical which is optionally substituted by halogen, $C_1$ to $C_4$ alkoxy, $C_1$ to $C_4$ alkylthio or $C_1$ to $C_4$ alkylamino and which has 1 to 20 carbon atoms, an optionally halogen-substituted $C_2$ to $C_5$ alkenyl or $C_2$ to $C_5$ alkinyl radical, a $C_3$ to $C_8$ cycloalkyl radical which is optionally substituted by $C_1$ to $C_4$ alkyl, $C_1$ to $C_4$ alkoxycarbonyl, phenoxybenzyloxycarbonyl and/or halogen, a phenyl-$C_1$ to $C_4$ alkyl radical which is optionally substituted by halogen, optionally halogen-substituted $C_1$ to $C_4$ alkyl or optionally halogen-substituted $C_1$ to $C_4$ alkoxy, a phenyl radical which is optionally substituted by halogen, nitro, $C_1$ to $C_4$ alkyl, optionally halogen-substituted $C_1$ to $C_4$ alkoxy, optionally halogen-substituted $C_1$ to $C_4$ alkylthio or trifluoromethyl and/or by optionally halogen-substituted $C_1$ or $C_2$ alkylenedioxy, or represents a furyl, thienyl or pyridyl radical, and
$R^1$ represents an optionally halogen-substituted radical selected from $C_1$ to $C_5$ alkyl, $C_2$ to $C_5$ alkenyl, $C_2$ to $C_5$ alkinyl, phenyl, benzyl, $C_1$ to $C_5$ alkoxy, phenoxy, benzyloxy, $C_1$ to $C_5$ alkylthio, $C_2$ to $C_5$ alkenylthio, $C_2$ to $C_5$ alkinylthio, phenylthio, benzylthio, $C_1$ to $C_5$ alkylamino (monoalkylamino or dialkylamino), phenylamino or benzylamino- and X represents oxygen or sulphur.

10. A process according to claim 1, in which

R represents a hydrogen atom, or an alkyl radical which is optionally substituted by fluorine, chlorine, methoxy, methylthio or dimethylamino and which has 1 to 10 carbon atoms, $C_2$ to $C_5$ alkenyl, a $C_3$ to $C_6$ cycloalkyl radical which is optionally substituted by chlorine and/or methyl, phenyl-$C_1$ or $C_2$ alkyl which is optionally substituted by chlorine or trifluoromethoxy, a phenyl radical which is optionally substituted by fluorine, chlorine, nitro methyl, methoxy, trifluoromethoxy, trifluromethyl and/or methylenedioxy or a thienyl or pyridyl radical, and $R^1$ represents an optionally fluorine-substituted or optionally chlorine-substituted radical selected from $C_1$ to $C_5$ alkyl, phenyl, $C_1$ to $C_5$ alkoxy, phenoxy, benzyloxy, $C_1$ to $C_5$ alkylthio, phenylthio, $C_2$ to $C_5$ alkenylthio, $C_2$ to $C_5$ alkinylthio, benzylthio and $C_1$ to $C_5$ alkylamino (monoalkylamino or dialkylamino), and X represents oxygen or sulphur.

11. A process according to claim 1, wherein such compound is O-ethyl-O-(1-cyano-2-methyl-propyl) thiophosphoric acid diester chloride of the formula

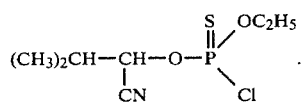

12. A process according to claim 1, wherein such compound is S-n-propyl-O-(1-cyano-2-methyl-propyl) dithiophosphoric acid diester chloride of the formula

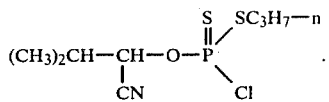

13. A process according to claim 1, wherein such compound is S-n-propyl-O-(1-cyano-2-phenyl-propyl) dithiophosphoric acid diester chloride of the formula

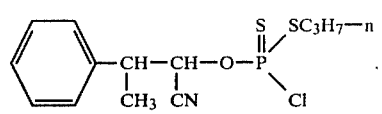

14. A process according to claim 1, wherein such compound is O-ethyl-O-(1-cyano-2-methyl-propyl) phosphoric acid diester chloride of the formula

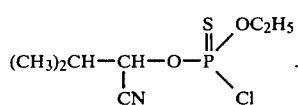

15. A process according to claim 1, wherein such compound is O-(1-cyano-2-methyl-propyl) benzenethiophosphonic acid ester chloride of the formula

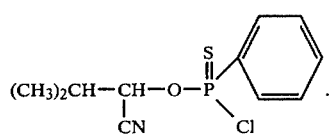

* * * * *

UNITED STATES PATENT AND TRADEMARK OFFICE
CERTIFICATE OF CORRECTION

PATENT NO. : 4,470,934

DATED : September 11, 1984

INVENTOR(S) : Bernd-Wieland Krüger et al

It is certified that error appears in the above-identified patent and that said Letters Patent is hereby corrected as shown below:

Col. 5, line 30  Delete "Müeller" and substitute --Müller--

Col. 12, line 23  Delete formula and substitute

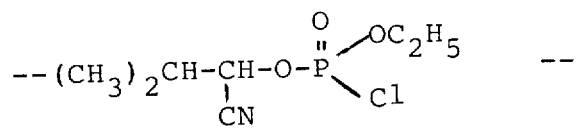

Signed and Sealed this

Twelfth Day of March 1985

[SEAL]

Attest:

DONALD J. QUIGG

Attesting Officer   Acting Commissioner of Patents and Trademarks